United States Patent
Lavía González et al.

(10) Patent No.: US 7,893,698 B2
(45) Date of Patent: Feb. 22, 2011

(54) NON-DESTRUCTIVE METHOD FOR DETECTING ZONES WITH NON CONDUCTIVE MATERIALS IN A COMPOSITE PART

(75) Inventors: Angeles Lavía González, Madrid (ES); Ignacio Manuel García Diego, Madrid (ES)

(73) Assignee: Airbus Espana, S.L., Madrid (ES)

( * ) Notice: Subject to any disclaimer, the term of this patent is extended or adjusted under 35 U.S.C. 154(b) by 440 days.

(21) Appl. No.: 12/182,373

(22) Filed: Jul. 30, 2008

(65) Prior Publication Data

US 2009/0289642 A1     Nov. 26, 2009

(30) Foreign Application Priority Data

May 23, 2008 (ES) ................................ 200801523

(51) Int. Cl.
*G01R 27/08* (2006.01)
*G01R 19/00* (2006.01)

(52) U.S. Cl. ........................ 324/717; 324/693; 324/724; 324/67

(58) Field of Classification Search ................... 324/67, 324/693, 713, 715, 717, 722, 724
See application file for complete search history.

(56) References Cited

U.S. PATENT DOCUMENTS

| 5,723,982 | A * | 3/1998 | Yasue et al. | 324/693 |
| 5,907,129 | A * | 5/1999 | Funaki et al. | 174/110 R |
| 6,967,499 | B1 * | 11/2005 | Haase et al. | 324/762.03 |
| 2003/0190470 | A1 * | 10/2003 | Ream et al. | 428/379 |

* cited by examiner

*Primary Examiner*—Timothy J Dole
(74) *Attorney, Agent, or Firm*—Ladas & Parry LLP

(57) ABSTRACT

Non-destructive method for detecting zones with non-conductive materials, such as materials that include glass fibers, in a part made of a conductive composite, such as a composite whose reinforcing fibers are carbon fibers, provided with an organic coating, that includes the following stages: a) providing a device for applying an electric potential on the surface of said part; b) determining the dielectric breakdown potential Pr corresponding to the thickness E of the coating; c) applying said dielectric breakdown potential Pr with said device to the part for the purpose of identifying those zones that have non-conductive materials when dielectric breakdown does not occur in them.

5 Claims, 2 Drawing Sheets

NON-DESTRUCTIVE METHOD FOR DETECTING ZONES WITH NON CONDUCTIVE MATERIALS IN A COMPOSITE PART

FIELD OF THE INVENTION

The invention relates to the field of manufacture of composite parts, i.e. parts manufactured from a composite material made up of a discontinuous fibre reinforcement and a continuous matrix of thermosetting resin and, more particularly, to a method of quality control of said parts and especially of those used in the aviation industry.

BACKGROUND OF THE INVENTION

The intensive introduction of advanced composites or composite materials in the primary structures of aircraft has become one of the priorities in the design and manufacture of a new generation of aircraft owing to the possibilities they provide for their structural optimization.

Without aiming to be exhaustive, the advantages of composites can be specified in three fundamental aspects:

Their high specific strength relative to metallic materials which is reflected in an advantageous strength/weight ratio.

Their excellent behaviour under fatigue loading.

The possibilities of structural optimization provided by the anisotropy of the material and the possibility of combining fibres with different orientations, permitting the design of elements with various mechanical properties, adapted to varying requirements in terms of applied loads.

One of the main advantages from the introduction of composites is the cost saving in assembly operations on account of the high degree of integration of structural elements that it permits. However, this high degree of integration demands adequate quality control.

One of the requirements that arises in the quality control of composite parts used in particular in the aviation industry is the detection of the existence of insulating materials in specific localizations of the parts when these materials are not visible because they are covered by paint or any other non-conductive organic coating.

In the prior art, destructive methods are used for this, such as abrasive methods for removing the organic coating and some of the non-conductive material to permit visual detection of the presence of said insulating materials.

In this specific aspect, as in many others, industry demands non-destructive methods, and the present invention is geared to meeting this demand.

The following terminology will be used in the description of the invention:

Part: Structural element to which the non-destructive method according to the present invention is applied, such as a structural element of an aircraft.

Conductive composite: The basic material used for the manufacture of the part, such as a carbon fibre composite.

Non-conductive material: Material used in the manufacture of the part to provide it with electrically insulating zones in some very precise localizations and of small combined dimension relative to the overall dimension of the whole part. An example of non-conductive material is a glass fibre composite.

Organic coating: protective layer applied to the part, after manufacture, such as a layer of paint.

SUMMARY OF THE INVENTION

One aim of the present invention is to provide a non-destructive method for detecting non-conductive materials in specific zones of parts made of a conductive composite, when these non-conductive materials are not visible because they are covered by a non-conductive organic coating.

Another aim of the present invention is to provide a method of quality control in the manufacture of parts from a conductive composite when the existence of electrically insulating zones is required in precise localizations of the part.

Another aim of the present invention is to provide a method capable of distinguishing between conductive composites and non-conductive materials and, in particular, capable of locating actual areas of non-conductive materials on conductive composites.

These and other aims are achieved with a non-destructive method for detecting zones with non-conductive materials in a part made of a conductive composite provided with an organic coating, that comprises the following stages:

a) Provide a device for applying an electric potential to said part.

b) Determine the dielectric breakdown potential Pr corresponding to the thickness of the coating.

c) Apply said dielectric breakdown potential Pr with said device to the part for the purpose of identifying those zones that have non-conductive materials when dielectric breakdown does not occur in them.

Other characteristics and advantages of the present invention will become clear from the following detailed description of an application illustrating its object, referring to the accompanying drawings.

DETAILED DESCRIPTION OF THE INVENTION

The method according to the present invention uses a technique based on the application of a potential and observation of the dielectric breakdown of the air or of a coating, with known uses for measuring thicknesses or detecting defects in organic coatings on metallic substrates and, in particular, for detecting defects in paint applied to metallic substrates, especially paint on pipes.

Now, as will be shown below, the method according to the present invention focuses on solving a problem very different from those that arise in the known methods: detection of the presence of a non-conductive material (such as a glass fibre composite), hidden under another different non-conductive material (the coating on the part to which the method is applied) when both are on a third conductive material (the basic component of the part to which the method is applied, typically a carbon fibre composite).

For application of the method, equipment is used that consists of a direct current source capable of supplying voltages in a predetermined range such as the Compact DC15 detector made by PCWI Technology Pty Ltd which has a sampling electrode formed from a brush of metal wires which are passed over the surface of the part to be tested.

A fundamental step in the method according to the invention is previous determination of the voltage to apply, i.e. the voltage that produces dielectric breakdown in the coating. When this voltage is applied in a zone in which there is glass fibre or some other non-conductive material underneath the coating, dielectric breakdown will not occur, and consequently an electric arc will not be observed. Accordingly, absence of an electric arc identifies the presence of non-conductive material.

Figure 1:
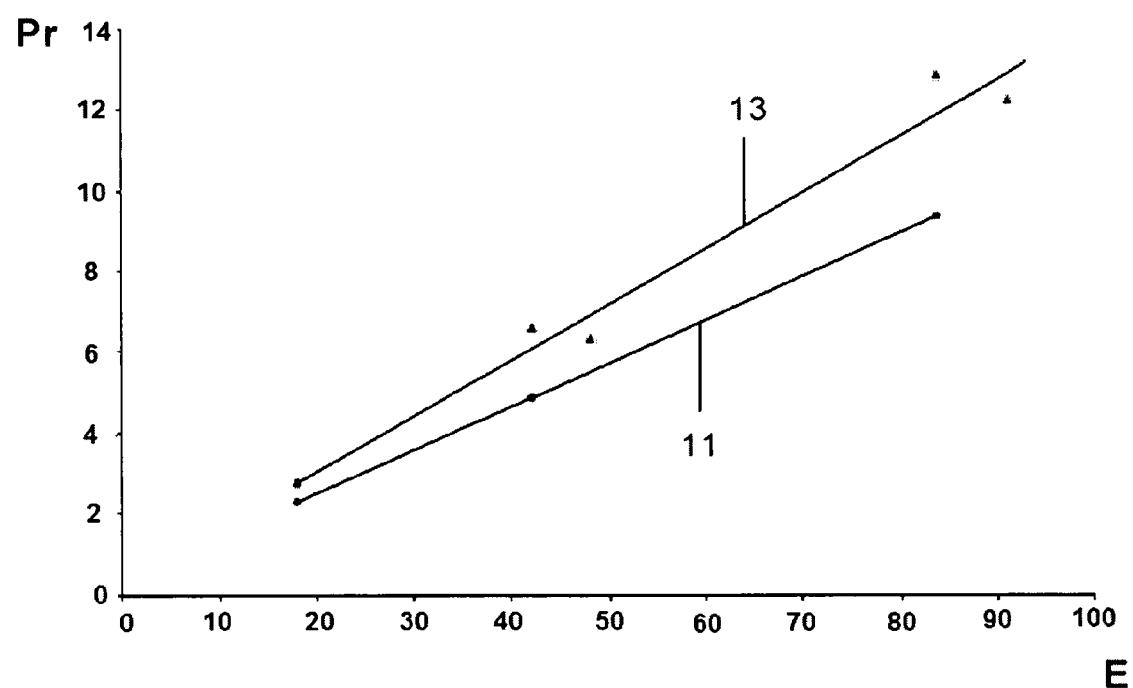
FIG. 1 is a graph showing the variation in dielectric breakdown potential of a given coating as a function of its thickness.

It was demonstrated in experiments that the dielectric breakdown potential Pr for a given coating is a linear function of its thickness E. In this connection, FIG. 1 shows two lines 11, 13 obtained by fitting, by the method of least squares, data from the experimental results for dielectric breakdown potentials (in kV) measured in composite parts of different thicknesses (in micrometres) on which primer Z12.129 was applied, using the aforementioned equipment. Line 11 relates to results obtained a month after application of the paint and line 12 relates to results obtained 8 months after application of the paint. It can be seen that ageing of the paint alters its dielectric resistance and consequently it is necessary to take account of the possible margin of error.

Figure 2A:
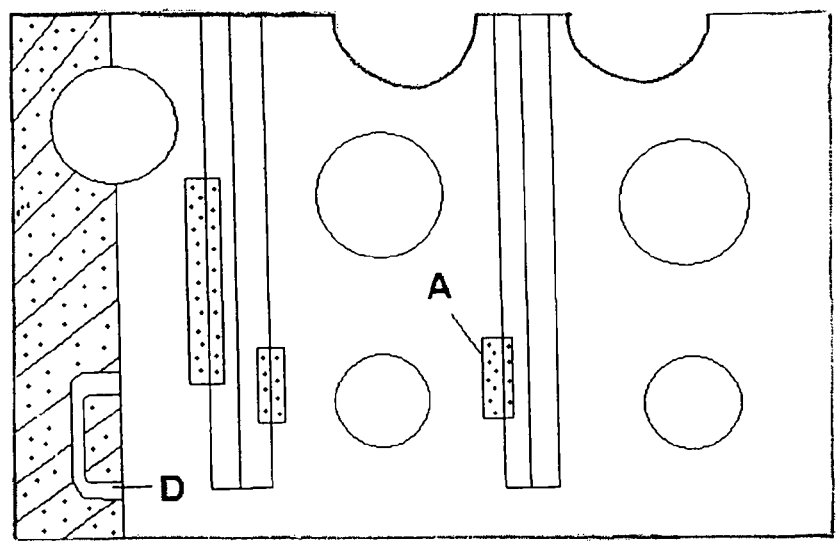
FIG. 2 shows schematically a test specimen used for testing the method according to the present invention.
Figure 2B:
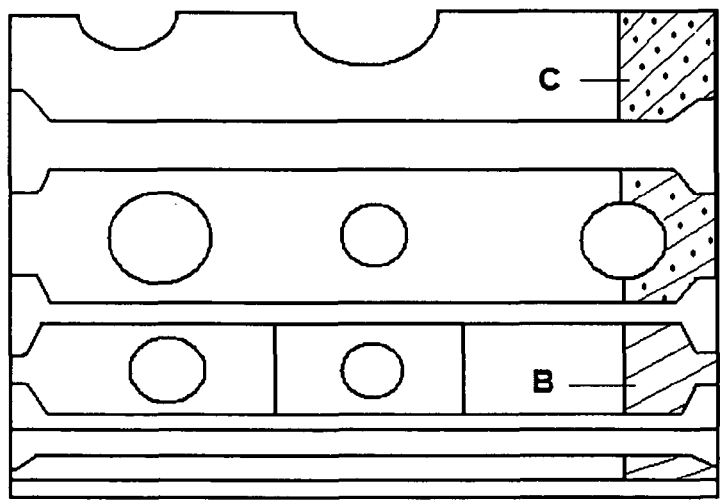

In the following we describe a test carried out on the composite test specimen shown schematically in FIG. 2 with the aforementioned equipment, the results of which confirm the effectiveness of the method of the present invention. Primer Z12.129 was used as the coating.

This test specimen contains several separate zones:
Zone A: Zone with glass fibre but without coating (delimiting its boundary with insulating tape).
Zone B: Zone without glass fibre but with coating.
Zone C: Zone with glass fibre and with coating.
Zone D: Zone in which glass fibre had been removed by sanding before priming.

In zones A, the potential was applied gradually up to the maximum potential without jumping of an electric arc on the glass fibre.

Next, on a zone B, the voltage was increased gradually until dielectric breakdown of the coating was produced, which occurred with a voltage of 4.5 kV.

Having fixed this potential as reference of the breakdown potential Pr for the thickness E of the coating on the test specimen, the electrode was applied in zones C, verifying that electric arcs were not produced.

Then, with this potential of 4.5 kV, the electrode was passed over zone D. Numerous electric arcs were produced, but not in the zones adjacent to where the glass fibre was maintained.

Moreover, said potential was also applied in the openings, where a protective layer of glass fibre has been placed. The result was that the glass fibre withstood said electric potential, but not the edges, where jumping of the electric arc occurred.

Modifications that are within the scope defined by the following claims can be made to the preferred embodiment that we have just described.

The invention claimed is:

1. Non-destructive method for detecting zones with non-conductive materials in a part made of a conductive composite provided with an organic coating, characterized in that it comprises the following stages:
   a) providing a device for applying an electric potential on the surface of said part;
   b) determining the dielectric breakdown potential Pr corresponding to thickness E of the coating;
   c) applying said dielectric breakdown potential Pr with said device to the part for the purpose of identifying those zones that have non-conductive materials when dielectric breakdown does not occur in them.

2. Method according to claim 1, characterized in that said dielectric breakdown potential Pr is obtained by applying, for each specific coating, a function that depends on the thickness E of the coating, established on the basis of data obtained in tests.

3. Method according to claim 1, characterized in that said conductive composite is a composite whose reinforcing fibres are carbon fibres.

4. Method according to claim 1, characterized in that said non-conductive material is a material that includes glass fibres.

5. Method according to claim 1, characterized in that said part is a structural element of an aircraft.

* * * * *